(12) United States Patent
Jackwood et al.

(10) Patent No.: US 6,569,629 B1
(45) Date of Patent: May 27, 2003

(54) GENE MARKERS FOR BEEF MARBLING AND TENDERNESS

(75) Inventors: Daral J. Jackwood, Wooster, OH (US); Francis Fluharty, Wooster, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 09/975,327

(22) Filed: Oct. 11, 2001

(51) Int. Cl.[7] .......................... C12Q 1/68; C12P 19/34; C07H 21/02; C07H 21/04
(52) U.S. Cl. .......................... 435/6; 435/912; 536/23.1; 536/24.31; 536/23.5; 536/24.33
(58) Field of Search ................... 435/6, 91.2; 536/23.1, 536/23.5, 24.31, 24.33

(56) References Cited

U.S. PATENT DOCUMENTS 6,242,191 B1    6/2001    Fluharty et al. ................ 435/6

FOREIGN PATENT DOCUMENTS

| WO | WO9953090 | * 10/1999 |
|---|---|---|
| WO | WO0069882 | * 11/2000 |

OTHER PUBLICATIONS

"Development and use of genetic markers to predict marbling and tenderness in beef cattle" by Fluharty, et al., 54th Annual Reciprocal Meat Conference, Jul. 24–18, 2001, Indianapolis, Indiana.

* cited by examiner

*Primary Examiner*—Carla J. Myers
(74) *Attorney, Agent, or Firm*—Calfee, Halter & Griswold LLP

(57) ABSTRACT

Methods and compositions are provided for objectively identifying: i) bovine animals having the genetic potential to produce beef that is marbled or tender, and ii) bovine carcasses whose beef is marbled or tender. The methods comprise extracting DNA from a sample obtained from a bovine animal or carcass, assaying for the presence of a DNA comprising a sequence, referred to hereinafter as a "genetic marker", in the DNA sample. In one aspect, the genetic marker is a marker of marbling, and comprises the sequence set forth in SEQ ID NO. 1. In another aspect, the genetic marker is a marker of tenderness, and comprises the sequence set forth in SEQ ID NO. 2, SEQ ID NO. 3, SEQ ID NO. 4 or combinations thereof. The compositions include primers that amplify markers of marbled or tender beef present in bovine animal or carcass genomes and hybridization probes to detect marbling or tenderness markers.

27 Claims, 6 Drawing Sheets

Fig. 1

5' TGCGGCGAACGACAACAAGGGGGTAAACGGGAAAGATCCCCCTTGGGGAGGGGTATTCAGTCAGAAGGTA
ATGGTTTCGAACAAAGACAAACCCTCTACCCCATCAGTGACCTGGAGGCAGTGAGGGGCCAGCCTG
AGAAATATTTCAGAAGGTAATTTACTTTTCTTTGGCAGGAGGATTTAATCTCTTAAAATGAGATTAAG
AAGGAGGGAAGGTTCTAGGTGATCCCTGTCTCTGGTCTGAGTAATTAGGTGAAAGGCAGTGATGTTTGCAGGA
AGAAAAAGATGAAAAGAACAGGTCTTGGGGTGATGACTCACGGTGCCAGTTATTCAGCGAGCACTTAG
AGAATTCCCAGTATGTGTTGGATGCTGTTTCAGGGAGTCATGACTGAGACAGGCAGAGTTCCTGCTCAT
GTGGCGAACAGAATGAAAAATGTAAAGAAGAATAAGAAGTTTCAATGATAAAGACCAAAATGAAGGATC
CAGGGAGTGATAGAGAATGAAAATGAGAAAGAAGAACATTCTAGGTCAGAGAAGTCCTCTTGGAGGACA
CACCATGTGAGCTGAGATGTGTACGGTTATCAGCTCTTCTGTGCTCGTTCGCGCA3'

Fig. 2

5' CGGGCAGGATGAGTGGTTCTAAGGCTGTCCGATCGCCTTGGAAATCACTTCGACCGT
GGCGCTGACTTGCTCTTGGTAACGGTCGAGTTCCTGCTGATGGTGCTTTTGCATTTCGA
TCTGCTCGGCGCACAGGTTCAGCGCCGCCAGCACCAATAGCTTGTCACCGATCAGCGTC
GGATACTTTTTCTTGGTGGTGGCCAGGGATGCCTTGAGCATCGTCACGGCGCTCATCAG
GGTGTTGTCTTCCCCTTCCGGTGCCTTGATCGAGTAATCCTCACCGAGAATCGAAACGA
CCTTTATCCCTTCATTCATGCGCTGACAGGACCTGCGCTCACACGCTCAACCAACGCCT
GGATACGGGCAGCGGTGGCGCCCTGCTTTTCTTCCTGCTCCATCAGGTTCAGCTGCAAG
CTGTCGTTTTCATCCTTGGCGCGAGCCAGTTCGGCCTTGAGGGATTCGTTGGTGCCCAG
CAGATCCTGGTTCTGCTGTACCAGGTCACTGACCAGTTGTTCCAATTGGCTGAGGGATG
CTTCTAACATTTTGATTTCTCGGCTTTTTCAAAGGGCGGTGACGATAAAGAAAAATCA
CCTCGGATGCCAGGGTTATCCCTGGCGCGGGGCCTTGATTTTACAGGGCAGGCCACGCT
TTCGAGCCTTAGTGACTGCATTTATGGCATCTGGTTCCTGAATCCCGTCGGACCGTCCC
GCACTGCGACAAAAGCGCGCACCCCTCAAGACTTTAGTCGTATGACCGATAGGTCATG
GACACCCCGCCCAAACCTCGCATGGATCGCGCTTCTCCCCAGGATCACAGCATGTCTCT
TCGTAATATGAATATCGCGCCGCGGGCCTTCCTCGGCTTCGCGTTGATTGGCGCGCTGA
TGTTGTTTCTCGGCGTGTTCGCGTTGAACCAGATGAGCAAGATTCGCGCGGCGACGGAA
GACATTACCCTCAGCAGCGTGCCGAGCATTCGCGCCCTGGACGAGTTCACCCAGCTGAC
CCTGCGCCTGCGGGTGCTGTCCTATCGCCTGCTGACCAACCGCGAGCCCGACGTCCAGC
AAAAGACCCTCGAAGCGTTTGATGTGCGCAATCAACAGATTCGTACCGCGCAGGCGGTC
TACGAGAAGCTGATCGACAGCAGCGAAGAGCGCGCCGCCTATGACGAGTACGTGCGTCT
TTTGGGCCAGTACCACCAGATCGAAGAACGCATGAAGAGCCTGTCCGGACCAATCAGG
TGGACGAACTGCGTACCCTGCTGAACACCGAGCTGCTGAACAACTCGGAACAGGTCAAC
GCCGTACTGAACCGCCTGCTGGACATCAATAACAAGATGGCCACCGCCACCAACCAGCA
AGCCGCCGACCAATACGACATGGCCTTTGAGCTGGTGGTGATCCTGCTGATCCTGCCCG
3'

Fig. 3

5' CGGGCAGGATTAGAGAAACTTAGAAGGGATTGCTGAAAACCCTGAGATTACAAACA
CCTGGAGGCCACCCCTGGGGCCTCAAGGGTCAAGGGGAGGAGGCAGGAGCACTCCTGG
AGCCCAGGGAGTGCCAAGGCAAGAGGGGAAGAGCCGTTGGCAGGAGCTGTGGCTGAGC
AGAGAAGCACTTCCACAGCCCCTGCCACCACGCAGAGAAGCCGTGGGCAAGAAATCCT
CCACCCTCTCCTCCCAGCCTCCAGCTGGCAGAGGCGTCCATTGATTCACTGCACAGGG
GGCAGCCTCCCAAGACACAGGTCGGGGCAAAGAAGGGGAGACCTGAGACCCTAAATTG
GAACAGACAAGCAGAGGATAACATCCTAGTACATCTCAATTCATTTTTTTTTTTCCCA
GAAGCCTCAGAAAGCTGAGGTGAACTTGCCCAAGGTCAGGCAGCAAGTTAGTGCAAGG
CCATTGGCCCCTCTCCCTCAGGGTCAAGGTTCATTAGATACTGGCCCTGCGCTGAAGC
AGCCAAGTAAAGATGGCCCGTTGTCCCAGAGCTGGAGCTGCAAATCCAAATTAGCCAG
AAGAAGACAGCAGAGTGGGGAGGATGGGCACGCAGGGCCGGCCATGCATCCTCTGT
GTCTGCACGGTAATAGACACCTGCCCG3'

Fig. 4

5' CGGGCAGGATACAGTGTGTTAACCGGGTTGAAGTCCCCAATCCATGAACATATTA
TAACTCTCCATTTTTTAGGTCTTTCTTGATTTCTTTCATGATTTTGTAGTTTTACGC
ACACATATTTTGCACATATTTTGTTAGATCTCTACCTGTGTTTTACCATTGGGATGA
CAGTTGTTAAAAAAGAAAGTATCAGTTTTCTGCTGGTGAATGGTAGAATATAGATAT
ATAATTTGGAGATTGACCTTCTTATGTCTTGAAACATTGCTAAATTTATTTTTCACT
TGTGGCTTTTTGACCTGCCCG3'

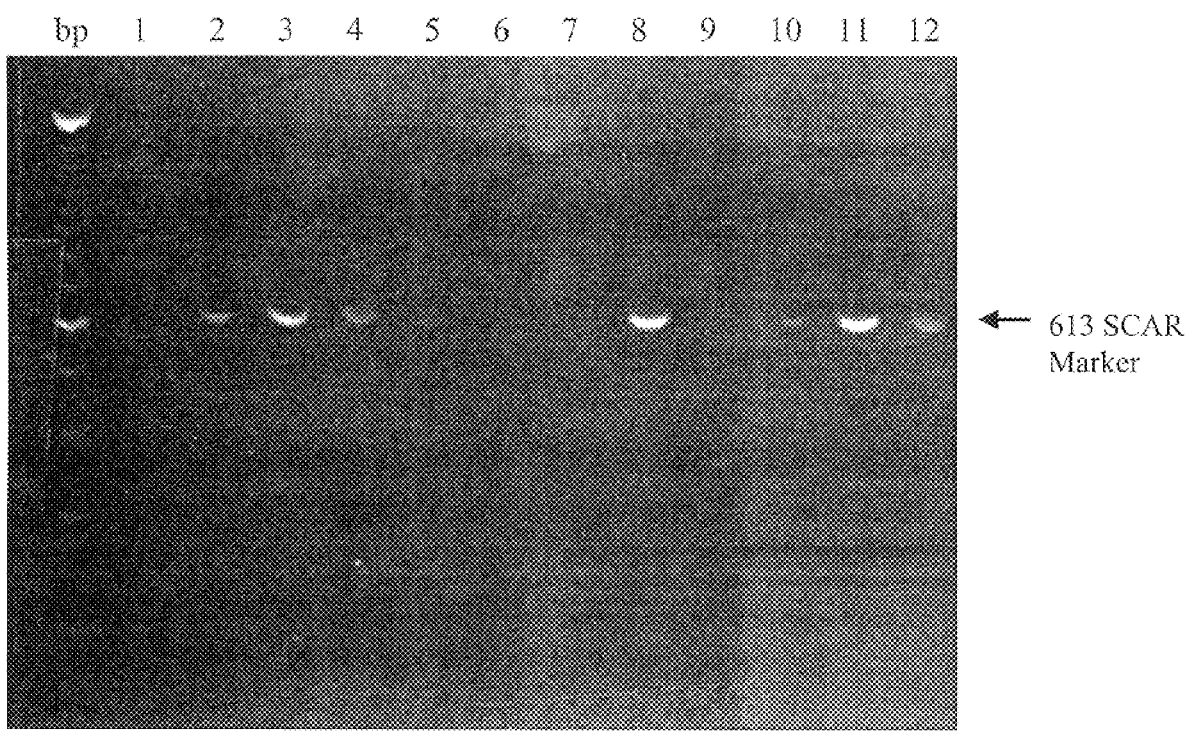

SEQUENCE LISTING

<160> NUMBER OF SEQ ID NOS: 13

<210> SEQ ID NO 1
<211> LENGTH: 613
<212> TYPE: DNA
<213> ORGANISM: Bos taurus

<400> SEQUENCE: 1

```
tgcgcgaacg acaacaaggg ggtaaacggg aaagatcccc ttggggaggg gtattcagtc      60
agaaggtaat ggtttcgaac aaagacaaac cctctacccc atcagtgacc tggaggcagt    120
gaggaggggc caggcctgag aaatatttca gaaggtaatt tacttttctt tggcaggagg    180
gattttaatc tcttaaaatg agattaagaa ggagggaagg ttctaggtga tcctgtctgg    240
tctgagtaat taggtgaaag gcagtgatgt ttgcaggaag aaaaaaagat gaaaagaaca    300
ggtcttgggg tgatgactca cggtgccagt tattcagcga gcacttagag aattcccagt    360
atgtgttgga tgctgtttca ggggagtcat gactgagaca ggcagagttc ctgctcatgt    420
ggcgaacaga atgaaaaatg taagaaggga ataagaagtt tcaatgataa agaccaaaat    480
gaaggatcca gggagtgata gagaatgaaa atgagaaaga aggaacattc taggtcagag    540
aagtcctctt ggaggacaca ccatgtgagc tgagatgtgt acggttatca gctcttctgt    600
gctcgttcgc gca                                                        613
```

<210> SEQ ID NO 2
<211> LENGTH: 1414
<212> TYPE: DNA
<213> ORGANISM: Bos taurus

<400> SEQUENCE: 2

```
cgggcaggat gagtggttct aaggctgtcc gatcgccttg gaaatcactt cgaccgtggc     60
gctgacttgc tcttggtaac ggtcgagttc ctgctgatgg tgcttttgca tttcgatctg    120
ctcggcgcac aggttcagcg ccgccagcac caatagcttg tcaccgatca gcgtcggata    180
cttttcttg gtggtggcca gggatgcctt gagcatcgtc acggcgctca tcagggtgtt    240
gtcttcccct tccggtgcct tgatcgagta atcctcaccg agaatcgaaa cgacctttat    300
cccttcattc atgcgctgac aggacctgcg ctcacacgct caaccaacgc ctggatacgg    360
gcagcggtgg cgccctgctt ttcttcctgc tccatcaggt tcagctgcaa gctgtcgttt    420
tcatccttgg cgcgagccag ttcggccttg agggattcgt tggtgcccag cagatcctgg    480
ttctgctgta ccaggtcact gaccagttgt tccaattggc tgagggatgc ttctaacatt    540
ttgatttctc gggctttttc aaagggcggt gacgataaag aaaaatcacc tcggatgcca    600
gggttatccc tggcgcgggg ccttgatttt acagggcagg ccacgctttc gagccttagt    660
gactgcattt atggcatctg gttcctgaat cccgtcggac cgtcccgcac tgcgacaaaa    720
gcgcgcaccc cctcaagact ttagtcgtat gaccgatagg tcatgacac cccgcccaaa    780
cctcgcatgg atcgcgcttc tccccaggat cacagcatgt ctcttcgtaa tatgaatatc    840
gcgccgcggg ccttcctcgg cttcgcgttg attggcgcgc tgatgttgtt tctcggcgtg    900
ttcgcgttga accagatgag caagattcgc gcggcgacgg aagacattac cctcagcagc    960
gtgccgagca ttcgcgccct ggacgagttc acccagctga ccctgcgcct gcgggtgctg   1020
tcctatcgcc tgctgaccaa ccgcgagccc gacgtccagc aaaagaccct cgaagcgttt   1080
gatgtgcgca atcaacagat tcgtaccgcg caggcggtct acgagaagct gatcgacagc   1140
```

| | |
|---|---|
| agcgaagagc gcgccgccta tgacgagtac gtgcgtcttt tgggccagta ccaccagatc | 1200 |
| gaagaacgca tgaagagcct gtcccggacc aatcaggtgg acgaactgcg taccctgctg | 1260 |
| aacaccgagc tgctgaacaa ctcggaacag gtcaacgccg tactgaaccg cctgctggac | 1320 |
| atcaataaca agatggccac cgccaccaac cagcaagccg ccgaccaata cgacatggcc | 1380 |
| tttgagctgg tggtgatcct gctgatcctg cccg | 1414 |

<210> SEQ ID NO 3
<211> LENGTH: 663
<212> TYPE: DNA
<213> ORGANISM: Bos taurus

<400> SEQUENCE: 3

| | |
|---|---|
| cgggcaggat tagagaaact tagaagggat tgctgaaaac cctgagatta caaacacctg | 60 |
| gaggccaccc ctgggcctc aagggtcaag gggaggaggc aggagcactc ctggagccca | 120 |
| gggagtgcca aggcaagagg ggaagagccg ttggcaggag ctgtggctga gcagagaagc | 180 |
| acttccacag cccctgccac cacgcagaga agccgtgggc aagaaatcct ccaccctctc | 240 |
| ctcccagcct ccagctggca gaggcgtcca ttgattcact gcacaggggg cagcctccca | 300 |
| agacacaggt cggggcaaag aagggagac ctgagaccct aaattggaac agacaagcag | 360 |
| aggataacat cctagtacat ctcaattcat ttttttttt cccagaagcc tcagaaagct | 420 |
| gaggtgaact tgcccaaggt caggcagcaa gttagtgcaa ggccattggc ccctctccct | 480 |
| cagggtcaag gttcattaga tactggccct gcgctgaagc agccaagtaa agatggcccg | 540 |
| ttgtcccaga gctggagctg caaatccaaa ttagccagaa gaagacagca gagtggggga | 600 |
| ggatgggcac gcagggggccg gccatgcatc ctctgtgtct gcacggtaat agacacctgc | 660 |
| ccg | 663 |

<210> SEQ ID NO 4
<211> LENGTH: 304
<212> TYPE: DNA
<213> ORGANISM: Bos taurus

<400> SEQUENCE: 4

| | |
|---|---|
| cgggcaggat acagtgtgtt aaccggttg aagtccccaa tccatgaaca tattataact | 60 |
| ctccattttt taggtctttc ttgatttctt tcatgatttt gtagttttac gcacacatat | 120 |
| tttgcacata ttttgttaga tctctacctg tgttttacca ttgggatgac agttgttaaa | 180 |
| aaagaaagta tcagtttct gctggtgaat ggtagaatat agatatataa tttggagatt | 240 |
| gaccttctta tgtcttgaaa cattgctaaa tttattttc acttgtggct ttttgacctg | 300 |
| cccg | 304 |

<210> SEQ ID NO 5
<211> LENGTH: 18
<212> TYPE: DNA
<213> ORGANISM: Bos taurus

<400> SEQUENCE: 5

| | |
|---|---|
| gcgcgaacga caacaagg | 18 |

<210> SEQ ID NO 6
<211> LENGTH: 19
<212> TYPE: DNA
<213> ORGANISM: Bos taurus

```
<400> SEQUENCE: 6
gcgcgaacga gcacagaag                                              19

<210> SEQ ID NO 7
<211> LENGTH: 20
<212> TYPE: DNA
<213> ORGANISM: Bos taurus

<400> SEQUENCE: 7
cgggcaggat gagtggttct                                             20

<210> SEQ ID NO 8
<211> LENGTH: 20
<212> TYPE: DNA
<213> ORGANISM: Bos taurus

<400> SEQUENCE: 8
ggcaggatca gcaggatcac                                             20

<210> SEQ ID NO 9
<211> LENGTH: 20
<212> TYPE: DNA
<213> ORGANISM: Bos taurus

<400> SEQUENCE: 9
cgggcaggat tagagaaact                                             20

<210> SEQ ID NO 10
<211> LENGTH: 20
<212> TYPE: DNA
<213> ORGANISM: Bos taurus

<400> SEQUENCE: 10
cgggcaggtg tctattaccg                                             20

<210> SEQ ID NO 11
<211> LENGTH: 20
<212> TYPE: DNA
<213> ORGANISM: Bos taurus

<400> SEQUENCE: 11
cgggcaggat acagtgtgtt                                             20

<210> SEQ ID NO 12
<211> LENGTH: 20
<212> TYPE: DNA
<213> ORGANISM: Bos taurus

<400> SEQUENCE: 12
cgggcaggtc aaaaagccac                                             20

<210> SEQ ID NO 13
<211> LENGTH: 10
<212> TYPE: DNA
<213> ORGANISM: Bos taurus

<400> SEQUENCE: 13
gcgcgaacga                                                        10
```

GENE MARKERS FOR BEEF MARBLING AND TENDERNESS

BACKGROUND

Beef used for human consumption has a number of characteristics desired by consumers. Characteristics such as color, texture, firmness, tenderness and marbling all contribute to the quality of a cut of meat. Based on such characteristics, the United States Department of Agriculture (USDA) classifies beef from bulls, steers and heifers into eight different quality grades. Beginning with the highest and continuing to the lowest, the eight quality grades are prime, choice, select, standard, commercial, utility, cutter and canner. Typically, beef that is classified as prime or choice is sold at higher prices than beef that is classified into lower quality grades.

One particularly desired characteristic of beef is marbling which refers to the relative amount of intramuscular fat in the beef. Well-marbled beef, i.e., beef that contains substantial amounts of intramuscular fat relative to muscle, tends to be classified as prime or choice; whereas, beef that is not marbled tends to be classified as select. Another desirable characteristic of beef desired by consumers is tenderness which refers to the softness or the ease in chewing the meat, after it is cooked.

At present, marbling is determined after a bovine animal is slaughtered. For example, marbling of beef from carcasses is determined by a certified USDA grader at the packing facility and involves visual inspection of a region between the 12th and 13th rib of a beef carcass. Unfortunately, the visual appraisal by the grader is costly, labor intensive, and time-consuming.

At present, tenderness of beef is determined after it has been cooked. Two methods are used. The first involves a subjective analysis by a panel of trained testers. The second is the Warner-Bratzler shear force procedure which involves an instrumental measurement of the force required to shear steaks, chops, and ground patties of cooked beef. Both methods are costly, time-consuming and can only be used to determine tenderness after the animals have been harvested and the beef has been cooked.

It is desirable to have alternative methods to determine if the beef obtained from a carcass is marbled or tender. Methods which are inexpensive, rapid and require minimal labor are especially desirable.

Also, it is desirable to have methods for determining if live animals have the potential to provide beef that is well-marbled and tender. There are numerous advantages in determining characteristics, marbling and tenderness for example, of beef from a live animal. One advantage is that an animal can be channeled into a particular feeding regimen or used to meet requirements of specific marketing programs based on the marbling and tenderness characteristics of the beef from that animal.

Another advantage of determining characteristics of beef from live animals is that these characteristics can indicate a "genetic potential" possessed by the live animal to pass, for example, its marbling and tenderness characteristics on to the animal's offspring. For example, an animal with advantageous marbling or tenderness genetic potential can be bred with other animals containing one or more markers of marbling or tenderness for the purpose of developing inbred lines of animals whose beef is particularly marbled or tender. Such inbred lines would provide beef products with known and consistent marbling and tenderness characteristics.

Unfortunately, there are a scarcity of methods for determining the characteristics of beef in live animals.

One recently developed method for determining both marbling and tenderness of beef, using samples from either live cattle or beef carcasses, is the method described in the commonly assigned U.S. Pat. No. 6,242,191 of Fluharty and Jackwood. This method comprises extracting DNA from a sample (e.g., blood) obtained from a bovine animal or beef carcass, amplifying the extracted DNA using specific primers under low stringency polymerase chain reaction (PCR) conditions to provide a pool of PCR products, and determining whether PCR products of specific sizes, which have been correlated with marbling or tenderness (i.e., marbling or tenderness markers), are present. The presence of the specific PCR products indicates that beef obtained from that animal or carcass will be marbled or tender, depending on which particular PCR products are present. The absence of the specific PCR products indicates that the beef obtained from that animal or carcass is not likely to be marbled or tender, also dependent on the particular PCR products present. This method, where PCR is performed under conditions where the specific primers bind to multiple specific locations within the extracted template DNA, such that a number of DNA sequences are amplified, is called a random amplified polymorphic DNA (RAPD) assay.

The RAPD assay is a vast improvement over earlier techniques. One advantage is that samples for testing can be obtained from live animals. Data obtained from such live-animal testing can be used to choose animals that should be interbred for the purpose of developing lines of bovine animals with the desired characteristics. Other advantages, in particular for testing of carcasses, is that the new method is objective and practical to perform on a large scale.

Although the RAPD assay is a major advance over what was previously available, it would be desirable to develop additional methods for testing beef. Such new methods would be specific, and possibly more easily adapted for use under various conditions. At the same time, it would be desirable to make these additional methods as simple to use as possible.

SUMMARY OF THE INVENTION

In accordance with the present invention, new methods are provided for objectively identifying: i) bovine animals having the genetic potential to produce beef that is marbled or tender, and ii) bovine carcasses whose beef is marbled or tender. The methods comprise extracting DNA from a sample obtained from a bovine animal or carcass, assaying for the presence of a DNA comprising a sequence, referred to hereinafter as a "genetic marker", in the DNA sample. Preferably, the assay is a quantitative assay which is capable of determining the number of copies of the genetic marker in the DNA sample. In one aspect, the genetic marker is a marker of marbling, and comprises the sequence set forth in SEQ ID NO. 1. In another aspect, the genetic marker is a marker of tenderness, and comprises the sequence set forth in SEQ ID NO. 2, SEQ ID NO. 3, SEQ ID NO. 4 or combinations thereof. In one embodiment the assay is a polymerase chain reaction (PCR) which employs primers that amplify all or a portion of SEQ ID NO. 1, SEQ ID NO. 2, SEQ ID NO.3, SEQ ID NO. 4, and the complements thereof.

The present invention also provides DNA sequences whose presence in the genome of a bovine animal or carcass indicates that the animal has the genetic potential to produce marbled or tender beef, and that beef from the animal or carcass has the potential to be marbled or tender. These sequences can be used to provide: i) primers that amplify markers of marbled or tender beef present in bovine animal or carcass genomes, ii) hybridization probes to detect marbling or tenderness markers, and iii) probes to detect RNA transcribed from marbling or tenderness markers.

The present invention also provides oligonucleotides comprising sequences from DNA whose presence in an animal or carcass genome correlates with beef marbling or tenderness. These oligonucleotides can be used as hybridization probes, PCR primers and DNA sequencing primers to detect marbling or tenderness markers.

The present invention also provides a kit that can be used for analyzing samples from a bovine animal or carcass for the presence of marbling or tenderness markers. The kit comprises DNA sequences, primers and primers sets that can be used to assay for the presence of marbling and tenderness markers in the genomes of bovine animals or carcasses.

BRIEF DESCRIPTION OF THE FIGURES

FIG. 1 shows the DNA sequence of a 613 nucleotide long RAPD fragment (SEQ ID NO. 1) that is a marker of marbling, where the bold, underlined sequence at the 5' end is SEQ ID NO. 5 and the bold, underlined sequence at the 3' end is the reverse complement of SEQ ID NO. 6; and FIG. 2 shows the DNA sequence of a 1414 nucleotide long RAPD fragment (SEQ ID NO. 2) that is a marker of tenderness, where the bold, underlined sequence at the 5' end is SEQ ID NO. 7 and the bold, underlined sequence at the 3' end is the reverse complement of SEQ ID NO. 8; and FIG. 3 shows the DNA sequence of a 663 nucleotide long RAPD fragment (SEQ ID NO. 3) that is a marker of tenderness, where the bold, underlined sequence at the 5' end is SEQ ID NO. 9 and the bold, underlined sequence at the 3' end is the reverse complement of SEQ ID NO. 10; and FIG. 4 shows the DNA sequence of a 304 nucleotide long RAPD fragment (SEQ ID NO. 4) that is a marker of tenderness, where the bold, underlined sequence at the 5' end is SEQ ID NO. 11 and the bold, underlined sequence at the 3' end is the reverse complement of SEQ ID NO. 12.

FIG. 6 shows agarose gel electrophoresis of samples following a real-time PCR reaction in SCAR marker analysis of cattle samples using the 613-1 (SEQ ID NO. 5) and 613-2 (SEQ ID NO. 6) primers.

DETAILED DESCRIPTION OF THE INVENTION

Figure 5:
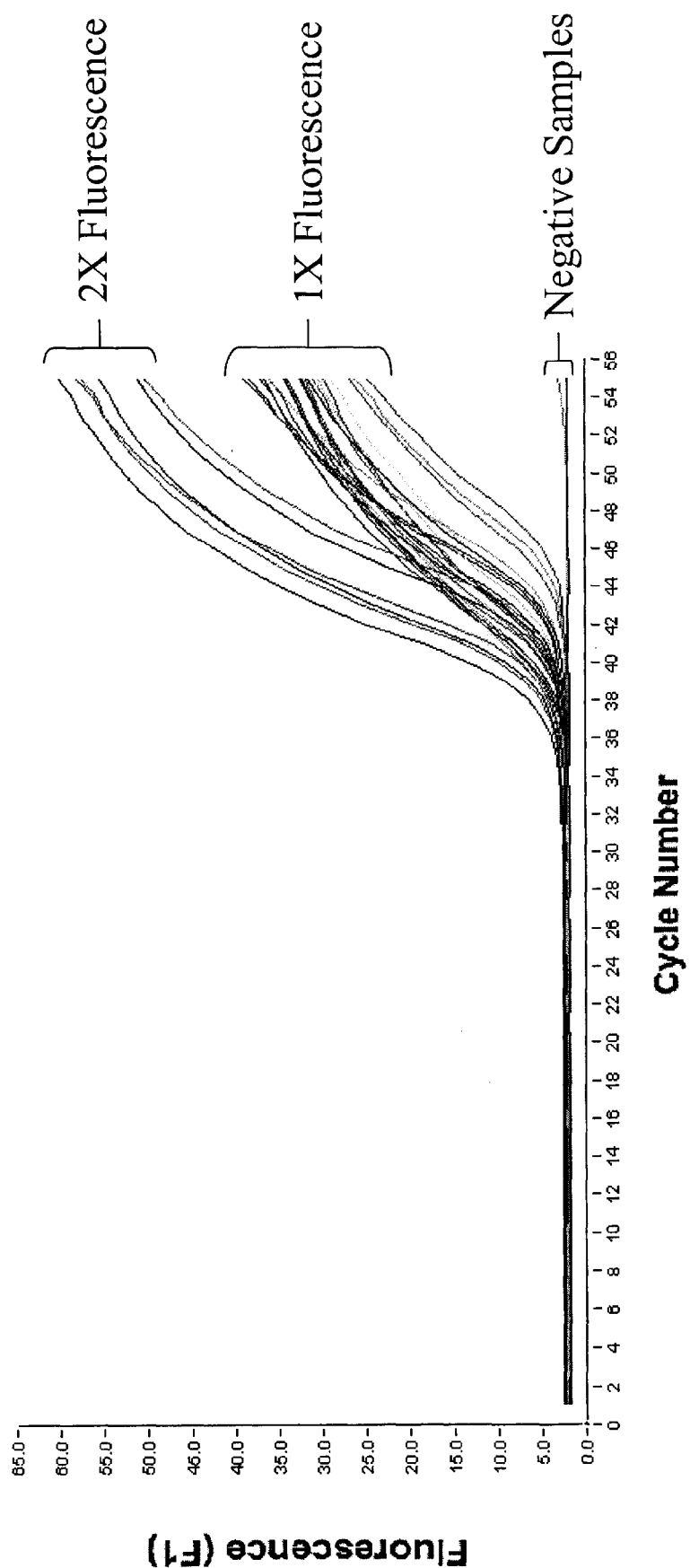
FIG. 5 shows fluorescence detected at each cycle of a real-time PCR reaction in SCAR marker analysis of cattle samples using the 613-1 (SEQ ID NO. 5) and 613-2 (SEQ ID NO. 6) primers.

The present invention provides DNA sequences or markers whose presence in the genomes of bovine animals or animal carcasses indicates that beef obtained from such animals or carcasses is likely to be highly marbled or tender. Herein, "markers" refers to gene sequences in the genomes of bovine animals indicating that beef from that animal is likely to have a particular characteristic. Herein, a marker of marbling is described whose presence in the genome of a bovine animal indicates that beef from that animal is likely to be marbled. Herein, markers of tenderness are described whose presence in the genome of a bovine animal indicates that beef from that animal is likely to be tender. Methods for detection of these markers are described and claimed in this application.

As used herein, the term "marbled" means beef that contains substantial amounts of intramuscular fat relative to muscle. As used herein, the term "tender" means beef that is soft and easily chewed after it has been properly cooked.

Herein, "genetic potential" refers to the likelihood that a bovine animal, having markers of beef marbling, or tenderness, or both marbling and tenderness in its genome, will pass those markers on to its offspring such that beef from the offspring will be marbled or tender.

DNA Sequences that Correlate with Beef Marbling

One DNA sequence or marker that correlates with marbling in beef is the 613 nucleotide sequence disclosed in FIG. 1 (SEQ ID NO. 1).

DNA Sequences that Correlate with Beef Tenderness

One DNA sequence or marker that correlates with tenderness in beef is the 1414 nucleotide sequence disclosed in FIG. 2 (SEQ ID NO. 2). Another sequence or marker that correlates with tenderness in beef is the 663 nucleotide sequence disclosed in FIG. 3 (SEQ ID NO. 3). Still another DNA sequence or marker that correlates with tenderness in beef is the 304 nucleotide sequence disclosed in FIG. 4 (SEQ ID NO. 4).

Preparation of Oligonucleotides and Polynucleotides

Oligonucleotides and polynucleotides comprising the DNA sequences disclosed in this application (SEQ ID NOS. 1–4) can be made in a number of ways. One way to make these oligonucleotides is to synthesize them using a commercially-available nucleic acid synthesizer. A variety of such synthesizers exist and are well known to those skilled in the art. Many such synthesizers use phosphoramidite chemistry, although other chemistries can be used. Phosphoramidite chemistry utilizes DNA phosphoramidite nucleosides, commonly called monomers, to synthesize the DNA chain or oligonucleotide. Such monomers are modified with a dimethoxytrityl (DMT) protecting group on the 5'-end, a b-cyanoethyl protected 3'-phosphite group, and may also include additional modifiers that serve to protect reactive primary amines in the heterocyclic ring structure (to prevent branching or other undesirable side reactions from occurring during synthesis).

To make a DNA molecule of a specific sequence, phosphoramidite nucleosides are added one-by-one in the 3'–5' direction of the oligonucleotide, starting with a column containing the 3' nucleoside temporarily immobilized on a solid support. Synthesis initiates with cleavage of the 5'-trityl group of the immobilized 3' nucleoside by brief treatment with acid [dichloroacetic acid (DCA) or trichloroacetic acid (TCA) in dichloromethane (DCM)] to yield a reactive 5'-hydroxyl group. The next monomer, activated by tetrazole, is coupled to the available 5'-hydroxyl and the resulting phosphite linkage is oxidized to phosphate by treatment with iodine (in a THF/pyridine/$H_2O$ solution). The above describes the addition of one base to the oligonucleotide. Additional cycles are performed for each base that is added. The final oligonucleotide added does not have a 5' phosphate. When synthesis is complete, the oligonucleotide is released from the support by ammonium hydroxide and deprotected (removal of blocking groups on nucleotides).

Normally, oligonucleotides of up to 150–180 bases long can be efficiently synthesized by this method using a nucleic acid synthesizer. To make polynucleotides that are longer than 100 bases, two single-stranded oligonucleotides, that are partially complementary along their length, can be synthesized, annealed to one another to form a duplex, and then ligated into a plasmid vector. Once a plasmid containing the ligated duplexes has been formed, additional oligonucleotide duplexes can be ligated into the plasmid, adjacent to the previously ligated duplexes, to form longer sequences. It is also possible to sequentially ligate oligonucleotide duplexes to each other, to form a long, specific sequence, and then clone the single long sequence into a plasmid vector.

Another way to make the polynucleotides comprising sequences disclosed in this application (SEQ ID NOS. 1–4) is to synthesize oligonucleotide primers (using the methodology described above) encoding sequences at the ends of each DNA sequence and use the primers in a PCR reaction to amplify the polynucleotide from a genomic template that contains the sequences. For polynucleotide sequence to be amplified, two primers are selected. Such primers are normally between 10 to 30 nucleotides in length. One primer is called the "forward primer" and is located at the left end of the sequence to be amplified. The forward primer is identical in sequence to the strand of the DNA shown in FIGS. 1–4. The forward primer hybridizes to the strand of the DNA which is complementary to the strand of the DNA shown in FIGS. 1–4. With reference to the sequences as oriented in FIGS. 1–4, the forward primer primes synthesis of DNA in a leftward to rightward direction.

The second primer is called the "reverse primer" and is located at the right end of the sequence to be amplified. The reverse primer is complementary in sequence to the strand of the DNA shown in FIGS. 1–4. The reverse primer hybridizes to the strand of the DNA shown in FIGS. 1–4. The reverse primer is the reverse complement of the strand of DNA shown in FIGS. 1–4. With reference to the sequences as oriented in FIGS. 1–4, the reverse primer primes synthesis of DNA in a rightward to leftward direction.

Using the primers, a genomic template DNA containing the sequences and an appropriate polymerase and buffer conditions, a standard PCR reaction, well-known to those skilled in the art, is performed. The PCR product that results comprises a sequence identical to SEQ ID NOS. 1–4 and can be cloned into a vector, a plasmid vector for example, and propagated in bacteria such as *Escherichia coli.*

A Method of Using the DNA Sequences to Analyze Beef Marbling and Tenderness

The DNA sequences shown in FIGS. 1–4 can be used in a variety of ways to determine whether a live animal has the genetic potential to produce beef that is marbled or tender. The DNA sequences can also be used in a variety of ways to objectively assess the marbling and tenderness characteristics of beef in a carcass. In one embodiment, the DNA sequences (SEQ ID NO. 1–4) are used to derive oligonucleotide primers that are used to amplify all or part of such DNA sequences present in the genome of a bovine animal or carcass using PCR. Amplification of such sequences produces so-called "sequence characterized amplified regions" (SCARS) (Paran and Michelmore, 1993, Theor Appl Genet, 85:985–93; Kaplan, et al., 1996, Mol Plant-Microbe Interact, 9:32–68; Maisonneuve, et al., 1994, Theor Appl Genet, 89:96–104; Ohmori, et al., 1996, Theor Appi Genet, 92:151–56). Each SCAR marker is amplified with specific primers and represents a single locus in the genome (Paran and Michelmore, 1993, Theor Appl Genet, 85:985–93; Abbasi, et al., 1999, Appl Environ Microbiol, 65:5421–6.). Such markers are defined genetically and, therefore, are physical landmarks in the genome.

To perform the SCAR assay, DNA is first obtained from a tissue sample or bodily fluid that contains cells, such sample coming from a bovine animal that is to be tested for the presence of the marbling or tenderness sequences. The bovine animal from which the tissue sample or bodily fluid is obtained can be alive or dead. A preferred sample from a live bovine animal is a blood sample. Another preferred sample is a saliva sample. Still another preferred sample, from a male bovine animal, is a semen sample. However, any sample that contains cells that contain DNA is acceptable. A preferred sample from a dead animal (i.e., a carcass) is muscle tissue which has been sliced from the carcass. Again, however, any sample from the carcass that contains cells that contain DNA is acceptable.

DNA is isolated or extracted from the cells contained within the tissue sample or bodily fluid. For example, DNA extraction may be performed using any of numerous commercially available kits for such purpose. One such kit, called IsoCode, is available from Schleicher and Schuell of Keene, N.H. The IsoCode kit contains paper filters onto which cells are applied. Through treatment of the paper filters as described by the manufacturer, most cellular components remain in the paper filter and DNA is released into an aqueous solution. The DNA in the solution can then be added to various enzymatic amplification reactions, as are discussed below.

Other commercially available kits exist for extraction of DNA from cells. Commercial kits do not have to be used, however, in order to obtain satisfactory DNA. Standard methods, well known to those skilled in the art, have been published in the scientific literature. Such methods commonly involve lysis of cells and removal of cellular components other than nucleic acids by precipitation or by extraction with organic solvents. Enzymatic treatment with proteases and ribonucleases can be used to remove proteins and RNA, respectively. DNA is then commonly precipitated from the sample using alcohol.

To assay the above described DNA for the presence of specific SCAR markers, target sequences which are located at the 5' and 3' ends of the sequences shown in FIGS. 1–4 are used to derive primers in the SCAR PCR assay (see the bold, underlined sequences in FIGS. 1–4). The use of such primers will result in amplification of the complete sequences shown in FIGS. 1–4. For each region to be amplified, two primers are selected. One primer is located at each end of the region to be amplified. Such primers will normally be between 10 to 30 nucleotides in length and have a preferred length from between 18 to 22 nucleotides. PCR primers can be selected to amplify the entire sequence shown in FIGS. 1–4, in which case primers are located at the 5' and 3' ends of the illustrated sequences. PCR primers can also be selected to amplify only a part of the sequences shown in FIGS. 1–4, in which case at least one of the two primers is located internal to the 5' and 3' ends of the illustrated sequences. The smallest such sequence that can be amplified is approximately 50 nucleotides in length (e.g., a forward and reverse primer, both of 20 nucleotides in length, whose location in the sequences in FIGS. 1–4 is separated by at least 10 nucleotides). Any sequence of approximately 50 nucleotides in length that is within the sequences shown in FIGS. 1–4 is within the scope of this application.

One primer is called the "forward primer" and is located at the left end of the region to be amplified. The forward primer is identical in sequence to the strand of the DNA shown in FIGS. 1–4. The forward primer hybridizes to the strand of the DNA which is complementary to the strand of the DNA shown in FIGS. 1–4. With reference to the sequences as oriented in FIGS. 1–4, the forward primer primes synthesis of DNA in a leftward to rightward direction.

The other primer is called the "reverse primer" and is located at the right end of the region to be amplified. The reverse primer is complementary in sequence to the strand of the DNA shown in FIGS. 1–4. The reverse primer hybridizes to the strand of the DNA shown in FIGS. 1–4. The reverse primer is the reverse complement of the strand of DNA shown in FIGS. 1–4. With reference to the sequences as oriented in FIGS. 1–4, the reverse primer primes synthesis of DNA in a rightward to leftward direction.

Preferably, the primers that are chosen to amplify a sequence within SEQ ID NOS. 1–4 are between 15 to 30 nucleotides in length, more preferably 18 to 25 in length, most preferably between 18 to 22 nucleotides in length.

PCR primers should also be chosen subject to a number of other conditions. PCR primers should be long enough (preferably 15 to 18 nucleotides in length) to minimize hybridization to greater than one region in the genomic template DNA. Primers with long runs of a single base should be avoided, if possible. Primers should preferably have a percent G+C content of between 40 and 60%. If possible, the percent G+C content of the 3' end of the primer should be higher than the percent G+C content of the 5' end of the primer. Primers should not contain sequences that can hybridize to another sequence within the primer (i.e., palindromes). Two primers used in the same PCR reaction should not be able to hybridize to one another. Although PCR primers are preferably chosen subject to the recommendations above, it is not necessary that the primers conform to these conditions. Other primers may work, but have a lower chance of yielding good results.

PCR primers that can be used to amplify DNA within a given sequence are preferably chosen using one of a number of computer programs that are available. Such programs choose primers that are optimum for amplification of a given sequence (i.e., such programs choose primers subject to the conditions stated above, plus other conditions that may maximize the functionality of PCR primers). One computer program is the Genetics Computer Group (GCG recently became Accelrys) analysis package which has a routine for selection of PCR primers. There are also several web sites that can be used to select optimal PCR primers to amplify an input sequence. One such web site is http://alces.med.umn.edu/rawprimer.html. Another such web site is http://www-genome.wi.mit.edu/cgi-bin/primer/primer3_www.cgi.

Once PCR primers are chosen, they are used in a PCR reaction. A standard PCR reaction contains a buffer containing 10 mM Tris-HCl (pH 8.3), 50 mM KCl, and 6.0 mM $MgCl_2$, 200 $\mu$M each of dATP, dCTP, dTTP and dGTP, two primers of concentration 0.5 $\mu$M each, 2 $\mu$l (75 ng/$\mu$l concentration) of template DNA and 2.5 units of Taq DNA Polymerase enzyme. Variations of these conditions can be used and are well known to those skilled in the art.

The PCR reaction is performed under high stringency conditions. Herein, "high stringency PCR conditions" refers to conditions that do not allow base-pairing mismatches to occur during hybridization of primer to template. Such conditions are equivalent to or comparable to denaturation for 1 minute at 95° C. in a solution comprising 10 mM Tris-HCl (pH 8.3), 50 mM KCl, and 6.0 mM $MgCl_2$, followed by annealing in the same solution at about 62° C. for 5 seconds.

Successful amplification of the template DNA to produce a PCR product of the correct size (i.e., a size equivalent to the length of the two primers plus the length of DNA between the two primers as shown in FIGS. 1–4) is determinative of whether the genome of the animal or carcass that is tested contains the sequence indicative of marbling or tenderness. Absence of a PCR product of the correct size indicates that the genome does not contain the sequence that is indicative of marbling or tenderness.

A particularly preferable aspect of the sequences shown in FIGS. 1–4 are present in two copies (i.e., be homozygous) in the diploid genomes of the bovine animal or carcass being tested. Genomes with two copies of sequences shown in FIGS. 1–4 are highly predictive of marbling or tenderness of the meat coming from that bovine animal or carcass. Genomes having two copies of the marbling or tenderness markers can be used to identify live bovine animals that will genetically transfer these markers to offspring through interbreeding. Genomes that have one copy (i.e., are heterozygous) of the sequences shown in FIGS. 1–4 are much less likely to be predictive of marbling or tenderness of meat from that animal or carcass. However, genomes having one copy of the marbling or tenderness markers can be used to identify live bovine animals that can be interbred to obtain animals having two copies of the markers. For example, heterozygous animals can be bred to homozygous animals to upgrade a herd of cattle. Genomes that have no copies of the sequences shown in FIGS. 1–4 are not predictive of marbling or tenderness.

A variety of methods can be used to determine if a PCR product has been produced. One way to determine if a PCR product has been produced in the reaction is to analyze a portion of the PCR reaction by agarose gel electrophoresis. For example, a horizontal agarose gel of from 0.6 to 2.0% agarose is made and a portion of the PCR reaction mixture is electrophoresed through the agarose gel. After electrophoresis, the gel is stained with ethidium bromide. PCR products are visible when the gel is viewed during illumination with ultraviolet light. By comparison to standardized size markers, it is determined if the PCR product is of the correct expected size.

In order for a PCR procedure, as described above, to be predictive of marbling or tenderness, the PCR procedure is done in such a way that the amount of PCR products can be quantified, and in a way that such quantity is determinative of whether the bovine animal or carcass genome from which the template DNA originates contains one or two copies of the particular sequence shown in FIGS. 1–4. Such "quantitative PCR" procedures normally involve comparisons of the amount of PCR product produced in different PCR reactions. For example, the presence of a given PCR product indicates that the genome from which the template DNA originates contains at least one copy of the particular sequence whose presence is being assayed. Among PCR reactions that contain the PCR product of interest, those PCR reactions that use template DNA from a genome containing two copies of the template, have twice the amount of PCR product as PCR reactions that use template DNA from a genome containing one copy of the template. Such determinations are normally made with the help of standardized PCR reactions wherein the template DNA is known to contain two, one or no copies of a sequence in the genome. A number of such quantitative PCR procedures, and variations thereof, are well known to those skilled in the art. One inherent property of all such procedures, however, is the ability to determine relative amounts of a sequence of interest within the template that is amplified in the PCR reaction.

One particularly preferred method of quantitative PCR used to quantify copy numbers of sequences within the PCR template is a modification of the standard PCR called "real-time PCR." Real-time PCR utilizes a thermal cycler (i.e., an instrument that provides the temperature changes necessary for the PCR reaction to occur) that incorporates a fluorimeter (i.e. an instrument that measures fluorescence). The real-time PCR reaction mixture also contains a reagent whose incorporation into a PCR product can be quantified and whose quantification is indicative of copy number of that sequence in the template. One such reagent is a fluorescent dye, called SYBR Green I (Molecular Probes, Inc.; Eugene, Oreg.) that preferentially binds double-stranded DNA and whose fluorescence is greatly enhanced by binding of double-stranded DNA. When a PCR reaction is performed in the presence of SYBR Green I, resulting DNA products bind SYBR Green I and fluorescence. The fluorescence is detected and quantified by the fluorimeter.

Other Methods of Using the DNA Sequences to Analyze Beef Marbling and Tenderness There are additional methods by which the DNA sequences shown in FIGS. 1–4 can be used to determine whether beef is marbled or tender. In one embodiment, the sequences or parts of the sequences shown in FIGS. 1–4 are used as hybridization probes against DNA isolated from bovine animals or carcasses. Hybridization of a probe to the DNA, under stringent hybridization conditions (i.e., conditions that do not allow mismatches during hybridization); see Example 6), indicates that the DNA contains the sequences indicative of marbling or tenderness. Using appropriate controls, which are known to those skilled in the art, such hybridization studies can be used to ascertain the genome copy number of the sequence detected.

Convenient methods for hybridization include, but are not limited to, Southern hybridization and dot blots. In Southern hybridization, the genomic DNA from an animal or carcass is digested with restriction endonucleases and the resulting fragments are then separated by size using agarose gel electrophoresis. After electrophoresis, the separated DNA fragments are blotted or transferred onto an appropriate membrane. Such membranes include, but are not limited to, nitrocellulose and nylon. After transfer of the DNA fragments to the membrane, the probe, which comprises all or part of SEQ ID NOS. 1–4, is labeled and hybridized to the separated DNA fragments on the membrane. The probe can be labeled by a variety of methods. A common label for the probe is radioactive phosphorus ($^{32}P$) which is often part of a nucleoside triphosphate that is incorporated into the DNA using an enzymatic reaction, such as nick translation, random primed labeling or end labeling. Hybridization of such a labeled probe to DNA fragments on a membrane is commonly detected using autoradiography. Other common methods for labeling DNA probes and detecting their hybridization includes, but is not limited to, non-radioactive methods, such as for example, chemiluminescent methods.

Another method for hybridizing a DNA probe to animal or carcass DNA is dot blotting. Dot blotting is very similar to Southern blotting except that the genomic DNA may not be digested with restriction endonucleases and the DNA is not run through an agarose gel. Rather, in dot blotting, genomic DNA from an animal or carcass is applied directly to a small area of a membrane. The labeled probe is then hybridized to the DNA on the membrane and hybridization is detected using the methods described above for Southern blotting.

Another group of methods where the DNA sequences in FIGS. 1–4 can be used to determine marbling or tenderness in beef includes methods where primers derived from SEQ ID NOS. 1–4 are used to synthesize DNA using the animal or carcass DNA as template. Determination of the sequence of the synthesized DNA (i.e., if it matches SEQ ID NOS. 1–4) is used to determine whether the genomic template DNA contains markers of marbling or tenderness. Various techniques exist to do this. In one technique, called the dideoxy method, a single primer is used to prime DNA synthesis. In another technique, two primers are used and DNA is amplified using PCR. The PCR products are then sequenced using any of a number of methods known to those in the art.

In a case where DNA from a bovine animal or carcass contains one or more of the sequences shown in FIGS. 1–4 and such sequences are transcribed into RNA, still other methods can be used to detect such transcripts which indicate that the DNA markers of marbling or tenderness are present in the DNA from the animal or carcass. Various methods can be used to detect such transcripts, many of which use all or part of a sequence shown in FIGS. 1–4 as a probe to hybridize to and indicate the presence of the RNA transcript.

One such method is known as Northern blot hybridization. In this method, RNA is isolated from bovine animals or carcasses and separated by size using gel electrophoresis. The RNAs in the gel are then transferred to a membrane, similar to the way in which DNA is transferred to membranes in Southern blotting. After transfer of the RNA to the membrane, a DNA sequence comprising all or part of SEQ ID NOS. 1–4, is labeled and hybridized to the RNA on the membrane. Hybridization of the DNA probe to RNA on the membrane is detected by autoradiography or chemiluminescence.

A variation of Northern blotting, analogous to the dot blotting technique described above, is called slot blotting or also dot blotting. In this technique, RNA isolated from an animal or carcass is applied directly to a membrane. The DNA sequence, comprising all or part of SEQ ID NO. 1–4, is then labeled and hybridized to the RNA on the membrane. Hybridization is detected by autoradiography or chemiluminescence.

Another method known in the art for using a DNA sequence to detect RNA transcribed therefrom is called S1 nuclease analysis. In this technique, a radioactively-labeled DNA fragment derived from all or part of SEQ ID NOS. 1–4 is hybridized to RNA isolated from a bovine animal or carcass under conditions where no mismatches occur. All DNA and RNA in the mixture that has not formed a DNA-RNA duplex is then degraded using nucleases and the remaining duplex is displayed after gel electrophoresis and autoradiography.

A variation of S1 nuclease analysis is called an RNase protection assay. In this assay, a region of SEQ ID NOS. 1–4 is used as a template for in vitro transcription and a radioactively-labeled RNA transcript is produced that is complementary to naturally occurring RNA that may be present in RNA isolated from a bovine animal or carcass. The in vitro transcribed RNA is hybridized to the RNA from the animal or carcass and RNA-RNA duplexes are detected after nuclease digestion, in a similar manner as described for the S1 nuclease assay above.

Uses of Marbling or Tenderness Detection in Animal or Carcass Genomes

Detection of markers for marbling or tenderness can be used in two ways, dependent upon whether the markers are detected in a sample taken from a live bovine animal or whether the sample is taken from an animal carcass.

If a sample from a live bovine animal is determined to contain one or more markers for marbling or tenderness, that animal can then be chosen for a particular use. For example, such an animal can be bred with other animals containing one or more markers for marbling or tenderness for the purpose of developing inbred lines of animals whose beef is particularly marbled or tender. Such an animal can also be channeled into particular feeding regimens or be used to meet the requirements of specific marketing programs.

Currently, certain purebred animals can have their projected marbling ability determined by expected progeny differences (EPD's) which are calculated within breeds of cattle such as Angus and Simmental, that use actual carcass data collected from offspring of sires and dams to predict the carcass characteristics of future offspring. This process is time consuming and costly, requiring the collection and analysis of carcass data from several offspring before sufficient reliability exists to accurately predict an animal's marbling ability or tenderness. Furthermore, reliable EPD's are only calculated on the most noteworthy sires within a given breed of cattle, and the calculation of EPD's with crossbred cattle (those whose parents are of different breeds) is highly unreliable. Because the majority of the nearly 30 million cattle fed annually in the United States are crossbreds without known parentage performance, EPD's have limited utility. Therefore, the use of EPD's is limited to purebred animals, and may be useful for mating selection, but not as a tool for making management decisions in the feedlot.

Ultrasound is used in the beef industry as a tool to enhance a feedlot operator's ability to market cattle at a desired end-point. However, it is only useful toward the end of the feeding period to determine an approximate harvest date. Producing consistently tender meat, and reducing excess external fat production while maintaining intramuscular fat deposition are three of the major challenges in the beef industry. Excessive back fat and internal seam, and kidney, pelvic, and heart (KPH) fat production causes inefficiencies in feedlots, due to the higher energy cost of depositing fat compared with protein, and the packing industry, due to the high cost of trimming and the low price received for the fat. Therefore, having the genetic information to develop feeding and management strategies to produce well-marbled, tender meat products is critical to the advancement of high-quality beef markets. For example, grid pricing systems pay based on the combination of USDA Quality and Yield grades. If feedlot operators knew that their cattle did not have the genetic ability to achieve the USDA Quality grade of Average Choice or above, those cattle could be fed to the Select or Low Choice Quality Grades and marketed before they had deposited backfat that would reach Yield Grades 4 (second highest grade or choice+) or 5 (highest grade or prime). They would then not receive discounts for excessive backfat, and could be managed in a more profitable manner.

In the purebred seedstock sector of the beef industry, markers for marbling or tenderness can be used in the following ways:

1. Sire selection can be based on actual genetic potential for desired consumer markets (i.e., either high-marbling or low-marbling branded programs or markets),
2. To develop lines of cattle with the genetic potential to produce offspring with tender meat regardless of the marbling potential, thus reducing consumer dissatisfaction with the consistency of the meat supply,
3. Offspring can be tested at birth for their genetic marbling and tenderness potential, and sire selection for the next mating can be done immediately, saving one to two generation intervals before genetic improvement can be made (currently, one to two additional matings occur before the carcass data is collected on the offspring). This occurs because cows are pregnant for 9 months, calves are weaned when they are approximately 7 months old, and are harvested usually between 15 to 24 months of age. Cows should give birth every year at approximately the same date. Therefore, they have a calf that is 3 to 4 months old, and the cows are still nursing the calf, when they are bred for the next calf crop (e.g., a cow gives birth in March, and the cow is re-bred in June). If carcass data is not collected on the March-born calf until it is 15 to 24 months of age, there will be, at best, a one generation loss before its carcass information is known. Many producers miss 2 generations of information, because sire selection is normally done in the winter months when producers have time to read and analyze the breed sire summaries. This loss of time is one of the major drawbacks to the use of EPD's.

In the commercial (not purebred) cow-calf sector and at feeder calf, markers for marbling or tenderness can be used in the following ways:

1. Sire selection can be based on producing feeder calves (calved destined for feedlots) for selected feeder calf sales aimed at specific types of feedlots (where calves are fed grain-based diets for 100 to 200 days prior to harvest),
2. Feeder calf auctions can use DNA tests to identify calves with the potential to reach distinct marbling and tenderness ranges. When combined with USDA feeder calf frame and muscle scores in calves marketed in lots with 50 to 100 pound weight ranges, the result will be very uniform groups of feeder calves both in and out of the feedlot. Thus, knowing the genetic potential of the calves purchased will help feedlots control uniformity and, therefore, increase potential profitability through enhanced management and marketing ability.

Benefits of using markers for marbling or tenderness on cattle entering the feedlot comprise the following:

1. Cattle can be fed according to their projected marbling ability,
2. There is no need to have Yield Grade 4 or 5 cattle, and their resulting marketing discounts, because their outcome weight and date could be projected by more than just "days on feed" or subjective appraisal of backfat,
3. This could be the end of the "Commodity Mix" and the beginning of a "Formalized Finished Cattle Market".

Potential benefits of using markers for tenderness on cattle carcasses at packing plants include:

1. The test for tenderness can be performed to determine those carcasses that are from cattle that are genetically "tough" regardless of their management prior to arrival at the plant. Those carcasses expected to produce tough meat can be segregated for further aging or processing so that the overall consistency of product leaving the plant is improved,
2. There is no loss of product with the genetic marker test, as there is with other tenderness tests that perform a costly, time-consuming Warner-Bratzler shear on steaks from selected carcasses.

Alternatively, if a sample from an animal carcass is determined to contain one or more markers for marbling or tenderness, beef from that carcass can be better and more easily classified into one of the USDA quality grades.

Although the invention has been described with regard to a number of preferred embodiments, which constitute the best mode presently known to the inventors for carrying out this invention, it should be understood that various changes and modifications as would be obvious to one having the ordinary skill in this art may be made without departing from the scope of the invention which is defined by the claims which are appended hereto.

EXAMPLES

The invention may be better understood by reference to the following examples, which serve to illustrate but not to limit the present invention.

Example 1
Detection of SEQ ID NO. 1 in Bovine Animal Genomes Using Real-Time PCR Genomic DNA was obtained from 191 animals that had been matched with respect to age and sex. Following harvest, USDA quality grade was determined according to the procedures set forth by the USDA. The animals exhibited five different degrees of marbling and were, thus, classified into five quality grades, including prime, choice+, choice·, choice−, and select. A numerical value was assigned to each of the grades, with the highest grade, i.e. prime, being assigned a numerical value of "5" and the lowest grade, i.e., select, being assigned a numerical value of "1".

Whole blood was collected from the jugular veins of these animals using a 16 ga needle and 10 ml syringe. Three drops of blood were placed onto Isocode filters (Schleicher and Schuell; Keene, N.H.) specially designed for PCR DNA samples. The filters were air-dried and stored at room temperature. A 1.0 mm×1.0 mm section of the Isocode filter, containing dried whole cattle blood, was placed in a 1.5 ml capped tube containing 0.5 ml of sterile water and mixed for 5 seconds. The filter section was removed, placed in a second 1.5 ml capped tube containing 0.5 ml of sterile water and mixed for 5 seconds. This washing procedure was repeated one more time.

After the third rinse, the filter section was placed in a 0.5 ml capped tube containing 0.2 ml of sterile water. The tube and contents were heated for 30 minutes at 95° C. After the 30 minute incubation, the filter section was removed and a 10 µl volume of the aqueous solution containing cattle DNA was used in a real-time PCR assay.

Primer sequences used in the PCR reaction were designed to amplify sequences shown in FIG. 1 (SEQ ID NO. 1). The forward primer was called 613-1 and had sequence 5'-GCGCGAACGACAACAAGG-3' (SEQ ID NO. 5). The reverse primer was called 613-2 and had sequence 5'-GCGCGAACGAGCACAGAAG-3' (SEQ ID NO. 6).

Real-time PCR was conducted using a LightCycler instrument (Idaho Technology Inc.; Idaho Falls, Id.) and LightCycler-DNA master SYBR Green I kit (Roche Molecular Biochemicals; Alamedia, Calif.). The reactions contained 2 µl 10×SYBR Green master mix (contains Taq DNA polymerase, reaction buffer, dNTP mix, and SYBR Green I dye), 6 mM $MgCl_2$, 0.5 µM of each primer, 2.0 µl of cattle DNA (75 ng/µl) and $H_2O$ was added to obtain a final reaction volume of 20 µl. The LightCycler reactions consisted of a denaturation step at 95° C. for 1 min and 55 cycles of denaturation at 95° C. for I sec, annealing at 62° C. for 5 elongation at 72° C. for 30 sec. A single fluorescence measure was taken after each elongation step and showed increasing fluorescence as PCR product was produced (FIG. 5). After about 55 cycles of the PCR reactions (i.e., following the log-linear phase), three groups of samples were observed and included samples with background fluorescence (absence of the 613 marker) samples with 1× fluorescence (heterozygous for the 613 marker) and samples with 2× fluorescence (homozygous for the 613 marker). Samples with 2× fluorescence had nearly twice the fluorescence as those samples with 1× fluorescence.

The 613 SCAR marker was observed in 103 (55%) of the 186 samples tested. This marker could also be used for segregating animals into groups that had 1× fluorescence (n=85), 2× fluorescence (n =18) or background fluorescence (n=83). Using Chi-Square analysis, a statistically significant difference was observed between animals with 2× fluorescence and those with 1× or background fluorescence. The statistical difference (p=0.02050) was observed when select and low choice cattle were compared to average choice and above. Eighteen or 9.7% of the animals had 2× fluorescence and of these animals 88.9% (n=16) were graded as average choice and above. A significant difference was not observed between 1× fluorescence or background fluorescence samples and-these quality grades. Furthermore, the number of cattle demonstrating background fluorescence and 1× fluorescence for the 613 SCAR marker was nearly identical, 44.6% and 45.7%, respectively.

Agarose gel electrophoresis of 12 of the above-described LightCycler products, each from a different animal, is shown in FIG. 6. By comparison with the 100 bp ladder size standards located in lanes labeled "bp", electrophoresis demonstrated that the primers were specifically amplifying DNA of the correct size (611 bp). The electrophoresis also demonstrated that samples 1, 5, 6, 7 and 9 did not contain the 613 marker, samples 2, 4, 10 and 12 represented 1× fluorescence (heterozygous for 613), and samples 3, 8 and 11 represented 2× fluorescence (homozygous for 613).

Following amplification, a melting curve was determined for the PCR product. The melting temperatures examined were from 60° C. to 95° C. The peak melting point of the 613 bp marker was approximately 85.5° C. Based on its nucleotide sequence, the calculated $T_m$ of the 613 bp marker was a nearly identical 86.0° C.

Example 2
Detection of SEQ ID NO. 2 in Bovine Animal Genomes Using Real-Time PCR Genomic DNA is isolated from a bovine animal or carcass is used in a real-time PCR reaction as described in Example 1 except that different PCR primers are used. The forward primer is called 1414-1 and has sequence 5'-CGGGCAGGATGAGTGGTTCT-3' (SEQ ID NO. 7). The reverse primer is called 1414-2 and has sequence 5'-GGCAGGATCAGCAGGATCAC-3' (SEQ ID NO. 8).

Agarose gel electrophoresis of the LightCycler products demonstrates that the primers are specifically amplifying DNA of the correct size (1412 bp).

Example 3
Detection of SEQ ID NO. 3 in Bovine Animal Genomes Using Real-Time PCR Genomic DNA is isolated from a bovine animal or carcass is used in a real-time PCR reaction as described in Example 1 except that different PCR primers are used. The forward primer is called 663-1 and has sequence 5'-CGGGCAGGATTAGAGAAACT-3' (SEQ ID NO. 9). The reverse primer is called 663-2 and has sequence 5'-CGGGCAGGTGTCTATTACCG-3' (SEQ ID NO. 10).

Agarose gel electrophoresis of the LightCycler products demonstrates that the primers are specifically amplifying DNA of the correct size (663 bp).

Example 4
Detection of SEQ ID NO.4 in Bovine Animal Genomes Using Real-Time PCR Genomic DNA is isolated from a bovine animal or carcass is used in a real-time PCR reaction as described in Example 1 except that different PCR primers are used. The forward primer is called 663-1 and has sequence 5'-CGGGCAGGATACAGTGTGTT-3' (SEQ ID NO. 11). The reverse primer is called 663-2 and has sequence 5'-CGGGCAGGTCAAAAAGCCAC-3' (SEQ ID NO. 12).

Agarose gel electrophoresis of the LightCycler products demonstrates that the primers are specifically amplifying DNA of the correct size (304 bp).

Example 5
PCR Amplification to Obtain and Clone SEQ ID NO. 1

Whole blood was collected from a bovine animal using a needle and syringe. Genomic DNA was isolated from the cells in the blood as described above in Example 1.

Ten µl of the DNA solution was used in a PCR reaction using a kit from Perkin Elmer Cetus of Norwalk, Conn. In addition to the DNA sample, each reaction contained 10 µl of 10×PCR buffer II, 200 µM each of dATP, dCTP, dGTP, dTTP, 2.5 mM $MgCl_2$, and 0.2 µM of a PCR primer with sequence 5'-GCGCGAACGA-3' (SEQ ID NO. 13). The total reaction volume was increased to 100 µl using sterile water. AmpliTaq DNA polymerase (2.5 units) was added to each reaction.

The assay was conducted in a Perkin Elmer thermal cycler. The reactions were initially incubated at 95° C. for 1 minute, followed by 40 cycles of denaturation at 95° C. for 1 minute, annealing at 37° C. for 1 minute 30 seconds, and elongation at 72° C. for 3 minutes Finally, the reactions were incubated at 72° C. for 7 minutes.

Ten µl of the PCR reaction mixture was run on a 2% agarose (FMC BioProducts; Rockland, Me.) gel in TNE buffer (10 mM Tris-HCl [pH 8.0], 100 mM NaCl, 1 mM ethylenediaminetetraacetic acid). After electrophoresis, the PCR products were visualized after staining of the gel with ethidium bromide and illumination with ultraviolet light. Sizes of the PCR products were determined by comparison to a 100 bp DNA ladder control from Promega, Corp. Madison, Wis.

The fragment of size approximately 600 nucleotides, containing SEQ ID NO. 1, was excised from the agarose gel and purified using a Geneclean Spin Kit (BIO 101; Vista, Calif.) according to the manufacturer's instructions. The fragment was adjusted to a concentration of 40 ng/µl and then ligated into the vector pGEM-T Easy (Promega). The ligation reaction contained ligation buffer (30 mM Tris-HCl, pH 7.8, 10 mM $MgCl_2$, 10 mM dithiothreatol, 1.0 mM ATP), 3.0 Units of T4 DNA ligase, 50 ng of pGEM-T Easy vector, and approximately 20 ng of the SEQ ID NO. 1 fragment. The reactions were incubated at 4° C. for 12 hours. Following incubation, the recombinant vectors were used to transform competent cells of the *E. coli* strain JM109 (Promega). Transformed cells were plated onto LB (Luria-Bertani) agar plates containing 100 µg/ml of ampicillin, 0.5 mM of IPTG (isopropyl-β-D-thiogalactopyranoside) and 50 mg/ml of X-Gal (5-bromo-4-chloro-3-indolyl-β-D-galactoside). Blue/white selection was used to identify bacterial clones containing plasmids with SEQ ID NO. 1 DNA inserts.

Bacterial clones containing plasmids with SEQ ID NO. 1 inserts were grown in LB containing 100 µg/ml ampicillin. Bacteria were collected by centrifugation from a 200 ml volume of broth culture and the plasmids were extracted using an alkaline lysis method (Maniatis, et al., 1982, Molecular Cloning (A Laboratory Manual), Cold Spring Harbor Press, Cold Spring Harbor, N.Y.).

Example 6
Southern Blotting Detection of Marbling or Tenderness Markers in DNA from a Bovine Carcass DNA is isolated from a muscle tissue sample that has been sliced from a bovine carcass. The tissue sample is cut into small pieces, added to a pre-cooled (using dry ice) mortar, and liquid nitrogen added. The tissue is then ground into a fine powder which is transferred to a clean tube. Nine ml of lysis buffer (50 mM Tris-HCl, pH 8.0, 50 mM EDTA, 1% SDS and 10 mM NaCl) is added to the tube and the powder is gently resuspended. One hundred µg of RNase A is added and the mixture is incubated at 37° for 1 hour. Then, 100 µl of a 10 mg/ml Proteinase K solution and the tube is incubated at 55° C. for between 1 and 18 hours. After incubation, 1 ml of 3 M Sodium acetate, pH 4.0 is added along with 10 ml of phenol and the tube is mixed gently and centrifuged until the phases separate. The phenol extraction step is repeated as above. The mixture is then extracted twice with a 24:23:1 mixture of phenol:chloroform:isoamyl alcohol. The clear upper phase is transferred to a new tube and precipitated with 2 volumes of cold ethanol. DNA is spooled on the end of a Pasteur pipette and resuspended in 2 to 5 ml of buffer.

Ten to 20 µg of DNA is digested with a restriction endonuclease, such as EcoRI and electrophoresed through a 0.8% agarose gel. The DNA in the gel is then denatured by incubating the gel for 30 minutes at room temperature in a solution of 0.5 M NaOH and 1.5 M NaCl. The gel is then rinsed in $H_2O$ and the DNA neutralized by incubation in a solution of 0.5 M Tris-HCl, pH 7.5, 1.5 M NaCl and 0.1 M EDTA.

Then, the DNA is blotted from the gel onto a nitrocellulose membrane. This is done by using 3 MM paper to wick 20×SSC (3 M NaCl, 0.15 M sodium citrate, pH 7.0) to a "sandwich" comprised of (from bottom to top) the agarose gel, pre-wetted nitrocellulose membrane, layer of 3 MM paper, stack of paper towels, and 500 g weight. Over 6 to 18 hours, the 20×SSC is drawn up through the gel, to the stack of paper towels and causes the DNA to transfer out of the gel onto the nitrocellulose. The membrane is then dried in air and irradiated by ultraviolet light to cross-link the DNA to the membrane.

The membrane is then pre-hybridized at 55° C. for 3 to 4 hours in a solution containing 6×SSC, 0.2% SDS, 0.1M EDTA and 5% dextran sulfate.

A DNA fragment of the sequence in SEQ ID NO. 1 (see Example 5) is radioactively labeled using the High Prime labeling kit from Roche Diagnostics (Berkeley, Calif.). This is done by taking 20 ng of DNA, boiling it to denature the strands, then placing the DNA on ice. The reactants of the High Prime kit, containing random oligonucleotide primers, nucleoside triphosphates, Klenow enzyme and appropriate reaction buffer, are added. Then, $^{32}P$-labeled dCTP is added and the mixture is incubated at 37° C. for 1 hour. The labeled DNA probe is then purified using a ProbeQuant G50 spin column (Amersham; Piscataway, N.J.) as described by the manufacturer. The purified, labeled probe is then heated to 100° C. for 5 minutes, added to the pre-hybridization mixture that is hybridizing to the membrane, and hybridized overnight at 55° C.

The next day, the membrane is removed from the hybridization solution and washed 3 times for 15 minutes at room temperature in 1×SSC and 0.1% SDS, and then 3 times for 15 minutes at room temperature in 0.1×SSC and 0.1% SDS. The membrane is wrapped in plastic wrap and exposed to X-ray film. After 4 days, the film is developed and bands on the autoradiogram, indicating hybridization of the probe to the sample DNA and presence of the SEQ ID No. 1 marker of marbling in the carcass.

What is claimed is:

1. A method of identifying a bovine animal or carcass having a genetic marker for marbled beef, comprising:
   (a) extracting DNA from cells in a sample obtained from the bovine animal or carcass to provide a DNA sample;
   (b) amplifying the DNA sample by a polymerase chain reaction (PCR) which employs a forward primer comprising at its 3' end a nucleotide sequence identical to at least 10 contiguous nucleotides within SEQ ID NO. 1 and a reverse primer comprising at its 3' end a nucleotide sequence fully complementary to at least 10 contiguous nucleotides within SEQ ID NO. 1,
   wherein said primers are selected to amplify a predetermined region of SEQ ID NO. 1, said region comprising 50 or more contiguous nucleotides within SEQ ID NO. 1, and wherein said primers
      i) do not contain runs of more than 5 of the same nucleotide base,
      ii) do not contain internal palindromic sequences,
      iii) do not hybridize to one another under stringent conditions, and
      iv) have 40 to 60 percent G+C content, and
      wherein said amplification provides a PCR product that is from 50 to 613 nucleotides in length; and
   (c) characterizing the size or the sequence of the PCR products,
      wherein the production of a PCR product having a size which is the same as the size of the predetermined region of SEQ ID NO. 1 or a sequence which is identical to or fully complementary to the sequence of the predetermined region of SEQ ID NO. 1 indicates that the animal or carcass has a genetic marker of marbling.

2. The method of claim 1, wherein the PCR primers are from 10 to 30 nucleotides in length.

3. The method of claim 2 the forward primer comprises a sequence at its 3' end which is identical to a sequence at or near the 5' end of SEQ ID NO. 1 and the reverse primer comprises a sequence at its 3' end which is fully complementary to a sequence at or near the 3' end of SEQ ID NO. 1.

4. The method of claim 3, wherein said forward primer is from 18 to 30 nucleotides in length and comprises at its 3' end the sequence set forth in SEQ ID NO. 5 and said reverse primer is from 18 to 30 nucleotides in length and comprises at its 3' end the sequence set forth in SEQ ID NO. 6.

5. The method of claim 1, wherein the PCR is quantitative PCR.

6. The method of claim 1, wherein the PCR is real-time PCR.

7. The method of claim 6, wherein the amount of PCR product produced in the PCR indicates that the cells from which the DNA was extracted contains two copies of SEQ ID NO. 1.

8. The method of claim 1, wherein the PCR product is characterized by determining the size of the PCR product.

9. The method of claim 1 wherein the PCR product is characterized by determining the sequence of the PCR product.

10. A method of identifying a bovine animal or carcass having a genetic marker for tender beef, comprising:
   (a) extracting DNA from cells in a sample obtained from the bovine animal or carcass to provide a DNA sample;
   (b) amplifying the DNA sample by a polymerase chain reaction (PCR) which employs a forward primer comprising at its 3' end a nucleotide sequence identical to at least 10 contiguous nucleotides within SEQ ID NO. 2, 3, or 4 and a reverse primer comprising at its 3' end a nucleotide sequence fully complementary to at least 10 contiguous nucleotides within SEQ ID NO. 2, 3, or 4, respectively,
   wherein said primers are selected to amplify a predetermined region of SEQ ID NO. 2, 3, or 4, respectively, said region comprising 50 or more contiguous nucleotides within SEQ ID NO. 2, 3, or 4, respectively, and wherein said primers
      i) do not contain runs of more than 5 of the same nucleotide base
      ii) do not contain internal palindromic sequences,
      iii) do not hybridize to one another under stringent conditions, and
      iv) have 40 to 60 percent G+C content, and
      wherein said amplification provides a PCR product that is from 50 to 1414, 663, or 304 nucleotides in length, respectively; and
   (c) characterizing the size or the sequence of the PCR products,
      wherein the production of a PCR product having a size which is the same as the size of the predetermined region of SEQ ID NO 2, 3, or 4, respectively, or a sequence which is identical to or fully complementary to the sequence of the predetermined region of SEQ ID NO. 2, 3, or 4 respectively, indicates that the animal or carcass has a genetic marker of tender beef.

11. The method of claim 10, wherein the PCR primers are from 10 to 30 nucleotides in length.

12. The method of claim 11 wherein the forward primer comprises a sequence at its 3' end which is identical to a sequence at or near the 5' end of SEQ ID NO. 2, SEQ ID NO. 3, or SEQ ID NO. 4, and the reverse primer comprises a sequence at its 3' end which is fully complementary to a sequence at or near the 3' end of SEQ ID NO. 2, SEQ ID NO. 3, or SEQ ID NO. 4, respectively.

13. The method of claim 4, wherein said forward primer comprises at its 3' end the sequence set forth in SEQ ID NO. 7 and said reverse primer comprises contains at its 3' end the sequence set forth in SEQ ID NO. 8.

14. The method of claim 11, wherein said forward primer comprises at its 3' end the sequence set forth in SEQ ID NO. 9 and said reverse primer comprises at its 3' end the sequence set forth in SEQ ID NO. 10.

15. The method of claim 11, wherein said forward primer comprises at its 3' end the sequence set forth in SEQ ID NO. 11 and said reverse primer comprises at its 3' end the sequence set forth in SEQ ID NO. 12.

16. The method of claim 10, wherein the PCR is quantitative PCR.

17. The method of claim 10, wherein the PCR is real-time PCR.

18. The method of claim 16, wherein the amount of PCR product produced in the PCR indicates that the cells from which the DNA was extracted contains two copies of SEQ ID NO. 2, SEQ ID NO. 3, SEQ ID NO. 4, or combinations thereof.

19. The method of claim 10, wherein the PCR product is characterized by determining the size of the PCR product.

20. The method of claim 10 wherein the PCR product is characterized by determining the sequence of the PCR product.

21. An isolated polynucleotide comprising a nucleotide sequence selected from the group consisting of SEQ ID NO. 1, SEQ ID NO. 2, SEQ ID NO. 3 and SEQ ID NO. 4.

22. A PCR product comprising a nucleotide sequence which is at least-50 nucleotides in length and is identical or fully complementary to 50 or more contiguous nucleotides found within SEQ ID NO. 1, SEQ ID NO. 2, SEQ ID NO. 3 or SEQ ID NO. 4.

23. A PCR primer pair, wherein one of the primers in said PCR primer pair comprises at least 15 contauous nucleotides of the sequence of SEQ ID NO. 5, SEQ ID NO. 7, SEQ ID NO. 9, or SEQ ID NO. 11 and wherein the other primer of said primer pair comprises at least 15 contauous nucleotides of the sequence of SEQ ID NO. 6, SEQ ID NO. 8, SEQ ID NO. 10, or SEQ ID NO. 12, wherein each of the primers in said PCR primer pair is from 15 to 30 nucleotides in length, and wherein said primer pairs amplify SEQ ID NO. 1, SEQ ID NO 2, SEQ ID NO. 3, or SEQ ID NO. 4, respectively under high stringency PCR conditions.

24. A kit for identifying bovine animals or carcasses whose DNA comprises a marker of beef marbling, one or more markers of beef tenderness or a marker of beef marbling and a marker of beef tenderness, said kit comprising:

(a) primers for amplifying a marker of marbling, said primers comprising a forward primer comprising at its 3' end a nucleotide sequence identical to at least 10 contiguous nucleotides within SEQ. ID. NO. 1 and a reverse primer comprising at its 3' end a nucleotide sequence fully complementary to at least 10 contiguous nucleotides within SEQ. ID. NO. 1, wherein said forward primer and said reverse primer are from 10 to 30 nucleotides in length and
   i) do not contain runs of more than 5 of the same nucleotide base,
   ii) do not contain internal palindromic sequences,
   iii) do not hybridize to one another under stringent conditions, and
   iv) have 40 to 60 percent G+C content; or (b) primers for amplifying one or more markers of tenderness, said primers comprising a forward primer comprising at its 3' end a nucleotide sequence identical to at least 10 contiguous nucleotides within SEQ. ID. NO. 2, SEQ. ID. NO. 3, or SEQ. ID. NO. 4, and a reverse primer comprising at its 3' end a nucleotide sequence fully complementary to at least 10 contiguous nucleotides within SEQ. ID. NO. 2, SEQ. ID. NO. 3, or SEQ. ID. NO. 4, respectively; wherein said forward primer and said reverse primer are from 10 to 30 nucleotides in length and
   i) do not contain runs of more than 5 of the same nucleotide base
   ii) do not contain internal palindromic sequences,
   iii) do not hybridize to one another under stringent conditions, and
   iv) have 40 to 60 percent G+C content; or (c) the primers of (a) and (b).

25. The kit of claim 24 wherein said primers are for amplifying a marker of marbling comprises at their 3' end the sequence of SEQ. ID. NO. 5 and SEQ. ID. NO. 6; and wherein primers for amplifying one or more markers of tenderness comprise at their 3' end the sequence of SEQ. ID. NO. 7 and SEQ. ID. NO. 8, SEQ. ID. NO. 9 and SEQ. ID. NO. 10, or SEQ. ID. NO. 11 and SEQ. ID. NO. 12.

26. A method of identifying a bovine animal or carcass having a genetic marker for marbled beef, comprising:

(a) extracting DNA from cells in a sample obtained from the bovine animal or carcass to provide a DNA sample;

(b) assaying said DNA sample by a Southern hybridization assay or dot blot assay which employs a hybridization probe that comprises a sequence identical or fully complementary to SEQ ID NO. 1, wherein hybridization of the hybridization probe to the DNA sample indicates that the bovine animal or carcass has a genetic marker for marbled beef.

27. A method of identifying a bovine animal or carcass having a genetic marker for tender beef, comprising:

(a) extracting DNA from cells in a sample obtained from the bovine animal or carcass to provide a DNA sample;

(b) assaying said DNA sample by a Southern hybridization assay or dot blot assay which employs a hybridization probe that comprises a sequence identical or fully complementary to SEQ ID NO. 2, SEQ, ID NO 3, SEQ ID NO. 4 or combinations thereof, wherein hybridization of the hybridization probe to the DNA sample indicates that the bovine animal or carcass has a genetic marker for tender beef.

* * * * *

UNITED STATES PATENT AND TRADEMARK OFFICE
CERTIFICATE OF CORRECTION

PATENT NO.   : 6,569,629 B1
DATED        : May 27, 2003
INVENTOR(S)  : Daral J. Jackwood and Francis Fluharty It is certified that error appears in the above-identified patent and that said Letters Patent is hereby corrected as shown below:

Column 23,
Line 37, after "2", please insert -- wherein --.
Line 52, after "claim", please delete "6" and insert -- 5 --.

Column 24,
Line 37, after "claim", please delete "4" and insert -- 11 --.

Column 25,
Lines 5 and 8, after "15", please delete "contauous" and insert -- contiguous --.

Signed and Sealed this

Second Day of September, 2003

JAMES E. ROGAN
*Director of the United States Patent and Trademark Office*